United States Patent
Noumi et al.

(10) Patent No.: US 12,392,600 B2
(45) Date of Patent: Aug. 19, 2025

(54) OPTICAL COHERENCE TOMOGRAPHY DEVICE AND OPTICAL COHERENCE TOMOGRAPHY METHOD

(71) Applicant: DAIKIN INDUSTRIES, LTD., Osaka (JP)

(72) Inventors: Masao Noumi, Osaka (JP); Atsushi Sakakura, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 68 days.

(21) Appl. No.: 18/187,791

(22) Filed: Mar. 22, 2023

(65) Prior Publication Data

US 2023/0228556 A1  Jul. 20, 2023

Related U.S. Application Data

(63) Continuation of application No. PCT/JP2021/034580, filed on Sep. 21, 2021.

(30) Foreign Application Priority Data

Sep. 23, 2020  (JP) .................................. 2020-158782

(51) Int. Cl.
*G01B 9/02091*  (2022.01)

(52) U.S. Cl.
CPC ................. *G01B 9/02091* (2013.01)

(58) Field of Classification Search
CPC ............ G01B 9/02091; G01B 9/02064; A61B 3/102; G01N 21/45; G01N 2021/1787; G01N 2201/0221; G01N 2201/08
See application file for complete search history.

(56) References Cited

U.S. PATENT DOCUMENTS 6,477,403 B1 *  11/2002  Eguchi ............... A61B 1/00172
                                                     600/478
6,788,861 B1  9/2004  Utsui et al.
(Continued)

FOREIGN PATENT DOCUMENTS

JP   2001-051225 A   2/2001
JP   2005-249704 A   9/2005
(Continued)

OTHER PUBLICATIONS

International Preliminary Report on Patentability dated Mar. 28, 2023 with a Translation of the Written Opinion of the International Searching Authority in Application No. PCT/JP2021/034580.
(Continued)

*Primary Examiner* — Jonathan M Hansen
(74) *Attorney, Agent, or Firm* — Sughrue Mion, PLLC

(57) ABSTRACT

An optical coherence tomography device, and an optical coherence tomography method using the optical coherence tomography device. The optical coherence tomography device includes an objective lens configured to focus light from a light source onto a sample and is configured to perform tomographic imaging of the sample based on interference between sample light, which is reflected light from the sample, and reference light, which is reflected light from a reference surface provided between the objective lens and the sample. The sample light and the reference light are each to pass through the objective lens. The objective lens is an Fθ lens.

11 Claims, 5 Drawing Sheets

(56) References Cited

U.S. PATENT DOCUMENTS

| | | | | |
|---|---|---|---|---|
| 2007/0081166 A1* | 4/2007 | Brown | ............... | A61B 3/1005 |
| | | | | 356/497 |
| 2011/0116045 A1 | 5/2011 | Utagawa | | |
| 2012/0136259 A1* | 5/2012 | Milner | ............... | A61B 1/00096 |
| | | | | 600/478 |
| 2013/0271757 A1 | 10/2013 | Kang et al. | | |
| 2015/0109622 A1 | 4/2015 | Ota | | |
| 2018/0164089 A1* | 6/2018 | Schönleber | ........ | G01B 9/02035 |
| 2018/0372478 A1* | 12/2018 | Chong | ............... | G01B 9/02057 |
| 2020/0049484 A1* | 2/2020 | Jensen | ................ | G01B 11/005 |
| 2020/0109938 A1 | 4/2020 | Jiang et al. | | |

FOREIGN PATENT DOCUMENTS

| | | |
|---|---|---|
| JP | 2011-104127 A | 6/2011 |
| JP | 2013-217700 A | 10/2013 |
| JP | 2015-017968 A | 1/2015 |

OTHER PUBLICATIONS

International Search Report for PCT/JP2021/034580 dated Nov. 9, 2021 (PCT/ISA/210).

Communication dated Dec. 18, 2024 issued by the European Patent Office in application No. 21872434.2.

V.-F. Duma, et al., "Handheld Scanning Probes for Optical Coherence Tomography", Romanian Reports in Physics, vol. 67, No. 4, 2015, pp. 1346-1358 (14 pages total).

* cited by examiner

OPTICAL COHERENCE TOMOGRAPHY DEVICE AND OPTICAL COHERENCE TOMOGRAPHY METHOD

CROSS REFERENCE TO RELATED APPLICATIONS

This application is a Rule 53(b) Continuation of International Application No. PCT/JP2021/034580 filed Sep. 21, 2021, claiming priority based on Japanese Patent Application No. 2020-158782, filed Sep. 23, 2020, the respective disclosures of all of which are incorporated herein by reference in their entirety.

TECHNICAL FIELD

The disclosure relates to optical coherence tomography devices and optical coherence tomography methods.

BACKGROUND ART

Optical coherence tomography (OCT) is mainly used for tomographic imaging of biological organs such as eyeballs in the medical field.

Typical optical coherence tomography devices are configured to split the light from a light source by, for example, a beam splitter, apply the resulting light beams separately to a sample and a reference mirror and obtain reflected light beams passed through respective optical paths, obtain the interference between these reflected light beams, and utilize the interference for tomographic imaging (for example, see Patent Literature 1).

CITATION LIST

Patent Literature

Patent Literature 1: JP 2011-104127 A

SUMMARY

The disclosure relates to an optical coherence tomography device including an objective lens configured to focus light from a light source onto a sample, the optical coherence tomography device being configured to perform tomographic imaging of the sample based on interference between sample light, which is reflected light from the sample, and reference light, which is reflected light from a reference surface provided between the objective lens and the sample, the sample light and the reference light each being to pass through the objective lens, the objective lens being an Fθ lens.

The disclosure can provide an optical coherence tomography device that is less likely to cause a shift in a tomographic image even in a portable form and that performs tomographic imaging over a wide area at one time, and an optical coherence tomography method using the device.

DESCRIPTION OF EMBODIMENTS

Figure 1:
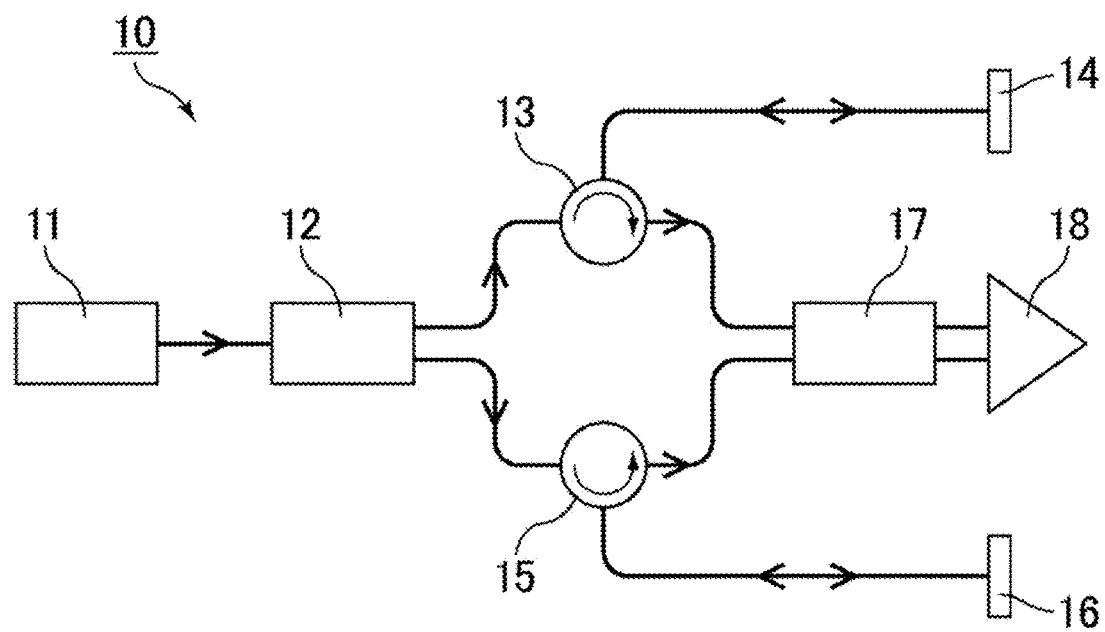
FIG. 1 is a schematic diagram of an example of a conventional optical coherence tomography (OCT) device.

In the medical field, an optical coherence tomography (OCT) device including a Michelson interferometer as shown in FIG. 1 is commonly used. An OCT device 10 of FIG. 1 is configured such that the light output from a light source 11 is split by a coupler 12 into reference light, which is to pass through an optical path including a circulator 13 and a reference mirror 14, and sample light, which is to pass through an optical path including a circulator 15 and a sample 16. The reference light and the sample light are recombined by a coupler 17 and an interference signal is detected by a photodetector 18.

In the medical field, a probe including the sample light path and an OCT device body (housing) including the reference light path are placed close to each other and are used in the same room in common cases.

In contrast, fields such as the industrial field may require imaging of an object placed far from the OCT device body (housing), e.g., in the open air, while a probe is carried. In this case, the Michelson OCT device shown in FIG. 1, in which the sample light and the reference light pass through the different optical paths, is likely to suffer difference in environmental conditions (e.g., temperature) under which the sample light path (probe) and the reference light path (body) are placed. This causes a difference between the optical path lengths, resulting in a great shift (drift) in a tomographic image obtained.

Further, OCT devices used in the medical field have a priority to provide a high-precision tomographic image of a very narrow area, such as an eyeball, and are difficult to apply to fields where tomographic imaging over a wide area at one time is required.

The disclosers performed studies to find that allowing both the sample light and the reference light to pass through the objective lens and using an Fθ (F-theta) lens as the objective lens can solve the above issues, completing the OCT device of the disclosure.

Hereinafter, the disclosure is described in detail.

The disclosure relates to an optical coherence tomography (OCT) device including an objective lens configured to focus light from a light source onto a sample, the optical coherence tomography device being configured to perform tomographic imaging of the sample based on interference between sample light, which is reflected light from the sample, and reference light, which is reflected light from a reference surface, provided between the objective lens and the sample, the sample light and the reference light each being to pass through the objective lens, the objective lens being an Fθ lens.

The OCT device of the disclosure is configured such that the sample light, which is reflected light from a sample to be imaged, and the reference light, which is reflected light from a reference surface, both pass through the objective lens. This structure can prevent difference in environmental conditions between the sample light path and the reference light path even when a portion including the objective lens (e.g., a probe) is in a portable form, resulting in a small shift in a tomographic image obtained.

The sample light and the reference light are to be incident on the objective lens through the surface close to the sample and are to be emitted therefrom through the surface close to the light source.

The sample light and the reference light are generated from the light from the light source. The light from the light source passes through the objective lens of the OCT device of the disclosure and focuses on the sample. The light reflected on the sample serves as the sample light. Part of the light from the light source is reflected on a reference surface provided between the objective lens and the sample, serving as the reference light.

The sample light and the reference light are each preferably generated from the light emitted from the light source and passed through the objective lens. In comparison with conventional Michelson OCT devices in which the light is split before passing through the objective lens to separately generate the sample light and the reference light, the above structure of the disclosure can reduce the difference in environmental conditions between the sample light path and the reference light path and can more greatly reduce the shift in a tomographic image obtained.

The objective lens of the OCT device of the disclosure is an Fθ lens. This structure enables tomographic imaging over a wide area at one time.

The Fθ lens is a lens that emits the incident light to the position apart from the optical axis by Fθ on the focal plane perpendicular to the optical axis, where f represents the focal length of the lens and θ represents the angle between the incident light and the optical axis of the lens.

The Fθ lens may be a telecentric Fθ lens or may be a non-telecentric Fθ lens.

The telecentric Fθ lens is an Fθ lens designed such that the main light beam is to be parallel to the optical axis of the lens, and is preferred in that it can provide a high-precision tomographic image even when the distance between the lens and a sample varies.

In the OCT device of the disclosure, the light beams passed through the objective lens are not necessarily incident on the sample in a telecentric manner. Still, in order to provide a tomographic image with a higher precision, the objective lens is preferably placed so that the light beams are incident on the sample in a maximally telecentric manner.

The reference surface is preferably provided between the objective lens and the sample perpendicularly to the optical axis of the objective lens.

The reference surface is any surface that reflects at least part of the light from the light source. In order to easily achieve a structure in which the sample light and the reference light pass through a common optical path, the reference surface is preferably a surface that transmits part of the light from the light source and reflects another part thereof. In this embodiment, the light transmitted through the reference surface focuses on the sample to generate the sample light, while the light reflected on the reference surface serves as the reference light.

The reference surface is preferably a flat surface of a reference item, more preferably the surface close to the sample of the reference item.

The reference item is preferably one that transmits part of the light from the light source and reflects another part thereof.

The material of the reference item may be a crystalline material, preferably a crystal that can be used for an optical window. Specific examples thereof include crystals of $MgF_2$, quartz ($SiO_2$), sapphire ($Al_2O_3$), $CaF_2$, $BaF_2$, LiF, and ZnSe. Owing to their excellent chemical resistance, preferred among these is at least one selected from the group consisting of $MgF_2$, $CaF_2$, quartz, and sapphire.

In a preferred embodiment, the reference surface is a flat surface of a reference item containing at least one selected from the group consisting of $MgF_2$, $CaF_2$, quartz, and sapphire.

The reference item is preferably one without any coating (e.g., coating for reflection control).

The reference item may have any shape including a flat surface, such as a plate shape, a cylindrical shape, or a prism shape, preferably a cylindrical shape. The cylindrical shape is not necessarily a perfectly circular cylindrical shape. In the case of a reference item including a different flat surface in addition to the reference surface, the reference surface and the different flat surface are not necessarily parallel to each other.

The reference item has a thickness (thickness in the optical axis direction) of preferably 1 to 50 mm, more preferably 10 to 30 mm.

In the case where the reference item has a non-uniform thickness, the thickness at the thinnest portion and the thickness at the thickest portion are each preferably within the above range.

The reference item preferably satisfies the following relation (1):

$$nd \geq Z_{max} \quad (1)$$

wherein nd represents the optical thickness of the reference item; and $Z_{max}$ represents the measurable distance.

The optical thickness is the product of the refractive index of the reference item and the actual (geometric) thickness.

The measurable distance is expressed by the following relation (2):

$$Z_{max} = c/(4\delta f) \quad (2)$$

wherein c represents the speed of light; and δf represents the frequency interval of OCT interference signal sampling.

Using a reference item satisfying the relation (1) can prevent appearance of a signal based on back reflection on the back bottom surface (the surface opposite to the reference surface) of the reference item in a tomographic image (within the area corresponding to a depth of not smaller than 0 but smaller than $Z_{max}$), which can provide a tomographic image with a higher precision.

The reference item more preferably satisfies the following relation (3):

$$n \times WD > nd > n \times Z_{max} \quad (3)$$

wherein n represents the refractive index of the reference item; WD represents the working distance of the OCT device; and nd and $Z_{max}$ are as defined above.

The working distance refers to the distance between the forefront surface close to the sample of the objective lens and the sample, with the lens being in focus.

Using a reference item satisfying the relation (3) can reduce the intensity of a ghost image based on back reflection on the back bottom surface (the surface opposite to the reference surface) of the reference item, which can provide a tomographic image with a higher precision.

In order to more reduce the intensity of a ghost image based on back reflection, the thickness of the reference item is preferably as thick as possible within the range satisfying the relation (3). Also, preferably, the back bottom surface of the reference item is tilted relative to the reference surface.

The aforementioned effect is particularly significant in the case of placing an anti-aliasing filter (low-pass filter) to be described later.

The reference item particularly preferably satisfies the following relation (4):

$$nd = m \times Z_{max} \quad (4)$$

wherein nd and $Z_{max}$ are as defined above; and m is an integer of 1 or greater.

In the formula, m is preferably an integer of 1 or greater and 20 or smaller, more preferably an integer of 1 or greater and 10 or smaller.

Using a reference item satisfying the relation (4) allows a signal based on back reflection on the back bottom surface (the surface opposite to the reference surface) of the reference item to overlap an edge of a tomographic image (the position corresponding to a depth of 0 or $Z_{max}$) and to less affect the tomographic image, which can provide a tomographic image with a much higher precision.

The OCT device of the disclosure may include the reference surface (reference item).

The OCT device of the disclosure is preferably configured to perform the tomographic imaging with the distance between the reference surface and the sample being 0 to 3 cm. Placing the reference surface and the sample close to each other in this way is preferred because this arrangement can lead to a short working distance, small noise, and a high resolution, as well as focusing at a deeper portion of the sample, resulting in a clearer tomographic image including a deeper portion. The OCT device of the disclosure includes an Fθ lens as the objective lens and can therefore perform high-precision tomographic imaging even when the reference surface and the sample are close to each other as described above.

Tomographic imaging may of course be performed with the distance between the reference surface and the sample being greater than the above.

The light source may be a low coherence light source, and is preferably a frequency-scanning light source configured to perform scanning while changing the frequency (wavelength) over time.

Examples of the frequency-scanning light source used include a wavelength-swept laser utilizing a wavelength-swept filter (e.g., driving with a polygonal mirror, driving with a galvanometer mirror), an FDML laser, a MEMS wavelength-swept light source (e.g., MEMS VCSEL, external cavity MEMS Fabry-Pérot laser), and an SGDBR laser.

Examples of the light beam output from the light source include visible light and infrared light. Near infrared light (NIR) is preferred. The light beam used is preferably a light beam having a wavelength of 800 to 2000 nm. In particular, from the viewpoint of stability of the light source and reliability of the sensor, more preferred is a light beam having a central wavelength of 940±50 nm, 1100±50 nm, 1310±50 nm, 1550±100 nm, or 1750±100 nm.

The OCT device of the disclosure may include the light source.

The OCT device of the disclosure performs tomographic imaging of the sample based on the interference between the sample light and the reference light. The interference may be any one that allows both the sample light and the reference light to theoretically pass through the objective lens, preferably Fizeau interference or Mirau interference, more preferably Fizeau interference.

Examples of OCT types to be used in the OCT device of the disclosure include time domain OCT (TD-OCT) and Fourier domain OCT (FD-OCT). Examples of the FD-OCT include spectral domain OCT (SD-OCT) and swept source OCT (SS-OCT). Owing to its high sensitivity and deep measurable depth, preferred among these is SS-OCT.

The OCT device of the disclosure preferably further includes a collimator configured to convert the light from the light source into parallel light. The collimator is preferably provided on the optical paths between the light source and the objective lens.

The OCT device of the disclosure preferably further includes a scanning mirror configured to scan the light emitted from the light source and focused on the sample. The scanning mirror is preferably provided on the optical path between the light source and the objective lens, and is more preferably provided on the optical path between the collimator and the objective lens.

Examples of the scanning mirror include a galvanometer mirror, a polygonal mirror, and a MEMS mirror. Preferred among these is a galvanometer mirror, more preferred is a single-axis or two-axis galvanometer mirror, still more preferred is a two-axis galvanometer mirror.

The OCT device of the disclosure preferably further includes a driver for driving the scanning mirror.

The OCT device of the disclosure preferably further includes a circulator configured to output the light from the light source toward the objective lens and output the sample light and the reference light passed through the objective lens toward a detector configured to detect the sample light and the reference light. In this embodiment, the sample light and the reference light can be transmitted by a single circulator. This configuration enables a smaller device and a lower cost than in the case of providing circulators separately for the sample light and the reference light as shown in FIG. 1.

The circulator preferably has three or more ports, more preferably has three ports.

The circulator is preferably provided on the optical path between the light source and the objective lens, more preferably provided on the optical path between the light source and the collimator.

In the case of a three-port circulator, the light from the light source is input to a first port close to the light source and output from a second port close to the objective lens. The sample light and the reference light passed through the objective lens are input to the second port and output from a third port close to the detector.

The OCT device of the disclosure preferably further includes a detector (also referred to as a detector (1)) configured to detect the sample light and the reference light. The detector (1) is preferably configured to detect an interference signal generated by the sample light and the reference light.

The detector (1) is preferably a differential photodetector. The detector (1) may have a function to amplify a signal. Alternatively, an amplifier may be provided separately.

The OCT device of the disclosure preferably further includes a coupler (also referred to as a coupler (1)) configured to split the light from the light source into split light 1 to be used for generating the sample light and the reference light and split light 2 to be used for removing a DC component of an interference signal. The coupler (1) is preferably provided on the optical path between the light source and the objective lens, more preferably provided on the optical path between the light source and the circulator.

The coupler (1), when provided, allows the split light 1 and the split light 2 to have an intensity ratio of preferably 90:10 to 99:1, more preferably 92:8 to 98:2. Light splitting with this intensity ratio enables effective removal of a DC component from an interference signal.

The OCT device of the disclosure preferably further includes a detector (also referred to as a detector (2))

configured to detect the split light 2. The detector (2) may be the same detector as the aforementioned detector (1) or may be a different detector.

The OCT device of the disclosure preferably further includes an attenuator configured to attenuate the split light 2. The attenuator is preferably a variable optical attenuator (VOA). The attenuator is preferably provided on the optical path between the coupler (1) and the detector (2) configured to detect the split light 2.

The OCT device of the disclosure preferably further includes a data acquisition (DAQ) system configured to acquire an interference signal generated by the sample light and the reference light. The DAQ system preferably includes an A/D converter. The DAQ system is preferably configured to convert the acquired interference signal into digital data.

The OCT device of the disclosure preferably further includes an anti-aliasing filter (also referred to as a low-pass filter) configured to attenuate unnecessary frequency components exceeding the measurable distance ($Z_{max}$). The anti-aliasing filter is preferably provided on the optical path between the detector (1) and the DAQ system described above.

The OCT device of the disclosure preferably further includes an arithmetic logic unit configured to generate an optical coherence tomographic image based on the interference signal generated by the sample light and the reference light. The arithmetic logic unit is configured to image the interference signal according to the properties such as the intensity to generate an optical coherence tomographic image.

The OCT device of the disclosure preferably further includes a display configured to display an optical coherence tomographic image obtained. The display may be of a stationary type or a portable type. A portable one is preferred because the image can be checked at the site where the image is obtained. The connection with the arithmetic logic unit may be wired or wireless. One display may be provided or multiple displays may be provided.

Figure 2:
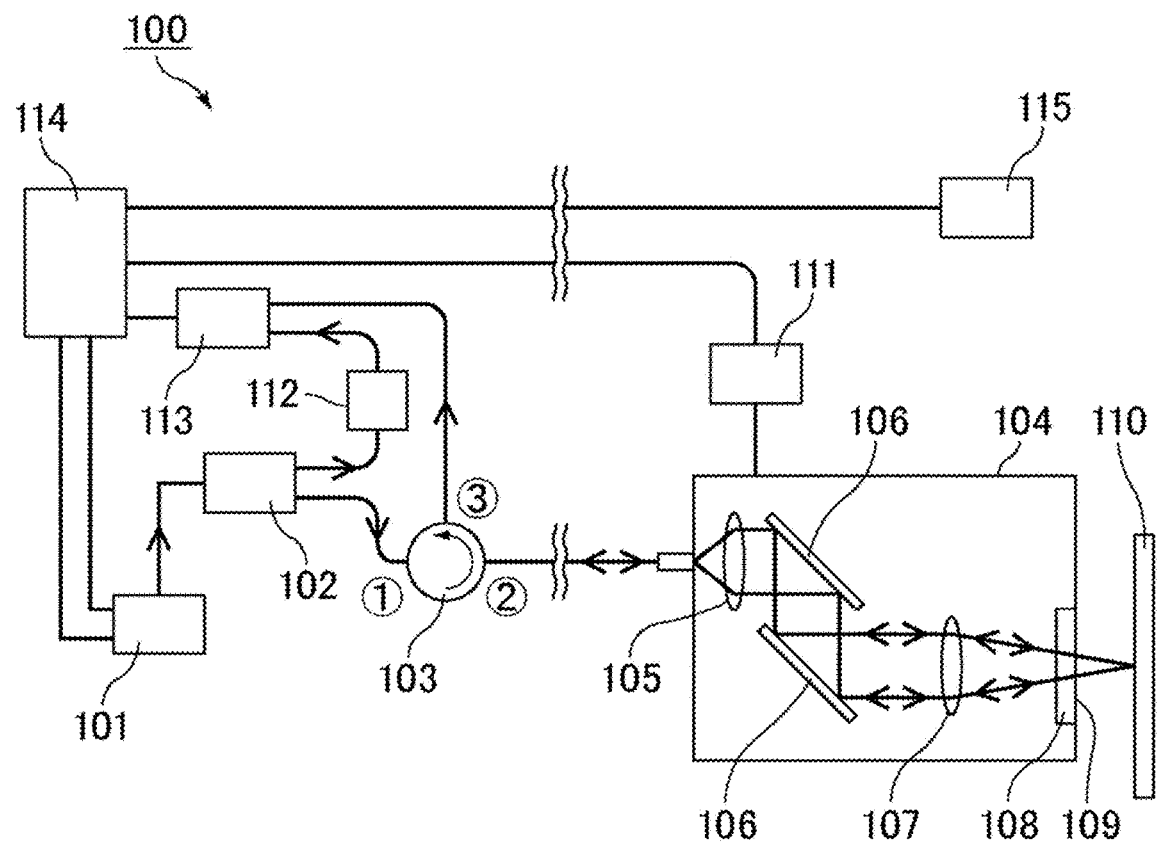
FIG. 2 is a schematic diagram of an example of the OCT device of the disclosure.

FIG. 2 shows an example of the OCT device of the disclosure. The OCT device of the disclosure is not limited thereto.

An OCT device 100 in FIG. 2 is configured such that a frequency-scanning light source 101 outputs the light to be used in OCT. The frequency-scanning light source 101 outputs a trigger signal at every start of frequency scanning. A Mach-Zehnder interferometer detects the light and outputs a K-clock signal for equal frequency interval sampling.

The light output from the frequency-scanning light source 101 is split by a coupler 102 into split light 1 to be used for generating sample light and reference light and split light 2 for removing a DC component of an interference signal at an intensity ratio of 95:5. The split light 1 is input to a port 1 of a circulator 103 and output from a port 2, and is transferred to a probe 104 through an optical fiber having a length of several meters.

In the probe 104, the split light 1 is converted by a collimator 105 into parallel light, which is then reflected on a galvanometer mirror 106 and incident on an objective lens 107, which is an Fθ lens. The galvanometer mirror 106 is driven by a galvanometer mirror driver 111 and scans the parallel light in the X-Y direction perpendicular to the optical axis. The parallel light incident on the objective lens 107 passes through a reference item 108 and focuses on a sample 110 to be imaged, and is then reflected on the surface of the sample and incident on the objective lens 107 as sample light. Part of the parallel light incident on the objective lens 107 is reflected on a reference surface 109 of the reference item 108 and then incident on the objective lens 107 as reference light.

The sample light and the reference light incident on the objective lens 107 pass through the galvanometer mirror 106 and the collimator 105, and are then input to a port 2 of the circulator 103 via the optical fiber, output from a port 3, and input to a differential photodetector amplifier 113. The differential photodetector amplifier 113 detects and amplifies the interference signal based on the interference between the sample light and the reference light.

The split light 2 generated by the coupler 102 is attenuated by a variable optical attenuator 112 and then input to the differential photodetector amplifier 113. The differential photodetector amplifier 113 utilizes the signal of the split light 2 to remove the DC component in the interference signal.

The amplified interference signal from which the DC component is removed by the differential photodetector amplifier 113 is collected and converted into digital data by the DAQ system (A/D converter) of a PC 114. Collection of the interference signal is initiated by a trigger signal emitted from the frequency-scanning light source 101 and synchronizes with the K-clock signal.

Between the differential photodetector amplifier 113 and the DAQ system is provided an anti-aliasing filter (not shown) that attenuates unnecessary frequency components exceeding the measurable distance ($Z_{max}$).

The arithmetic logic unit of the PC 114 generates an optical coherence tomographic image of the sample 110 based on the interference signal converted by the DAQ system and displays it on a mobile display 115.

The OCT device of the disclosure is preferably configured to enable the tomographic imaging while a user carries a portion including the objective lens. Even in such a case where the portion including the objective lens is in a portable form, the OCT device of the disclosure can prevent difference in environmental conditions between the sample light path and the reference light path, resulting in a small shift in a tomographic image obtained.

The portion including the objective lens preferably further includes the reference surface (or the reference item), the collimator, and the scanning mirror.

The portion including the objective lens is preferably a probe of the OCT device.

The OCT device of the disclosure is preferably configured to enable the tomographic imaging while a user holds the portion including the objective lens in hand(s), more preferably to enable the tomographic imaging while a user holds the portion including the objective lens in one hand.

The OCT device of the disclosure may further include a portion that may be carried by a user during tomographic imaging in addition to the portion including the objective lens. Examples of this carriable portion include a driver for driving the scanning mirror and the display.

The OCT device of the disclosure is preferably such that the portion including the objective lens to be carried and a portion not to be carried are connected via an optical fiber and that the light from the light source as well as the sample light and the reference light are transferred through the optical fiber. In this embodiment, an object to be imaged, which is placed far from the portion not to be carried, can be subjected to tomographic imaging by adjusting the length of the optical fiber so that the portion including the objective lens is placed near the object to be imaged. Since the light from the light source as well as the sample light and the reference light are transferred through the optical fiber, no difference in environmental conditions occurs between the sample light path and the reference light path even when the optical fiber is long, resulting in a small shift in a tomographic image obtained. Further, since the device is wired with the optical fiber, an object to be imaged placed far from the portion not to be carried can also be subjected to high-resolution OCT measurement.

The optical fiber may have any length in accordance with the place of an object to be imaged. The length may be 1 m or longer, preferably 3 m or longer, more preferably 5 m or longer, still more preferably 10 m or longer, while it may be 100 m or shorter, or may be 50 m or shorter.

For example, the portion not to be carried preferably includes the light source, the circulator, the detector, the DAQ system, the arithmetic logic unit, and the like.

The portion not to be carried is preferably an OCT device body (housing).

In the case where a different carriable portion is present in addition to the portion including the objective lens, this different portion and the portion including the objective lens or the portion not to be carried may be connected not necessarily via an optical fiber. They may be connected via an electric wire.

The OCT device of the disclosure is preferably such that an optical coherence tomographic image obtained has a shift of 100 μm or smaller when the optical fiber has a length of 3 m or longer and the atmosphere around the portion including the objective lens to be carried and the atmosphere around the portion not to be carried have a temperature difference of 1° C. or greater.

In fields such as the industrial field, an object to be imaged may be placed far from the OCT device body (housing), in the open air, or in a high- or low-temperature facility. In these cases, a great difference in environmental conditions (temperature) occurs between the probe and the OCT device body. Thus, an OCT device including the sample light path on the probe end and the reference light path on the body end provides a tomographic image with a great shift due to the difference in environmental conditions between the sample light path and the reference light path. In contrast, even in the above case, the OCT device of the disclosure causes no difference in environmental conditions between the sample light path and the reference light path, resulting in a small shift in a tomographic image obtained.

In the above embodiment, the length of the optical fiber is preferably 3 m or longer, more preferably 5 m or longer, still more preferably 10 m or longer, while it may be 100 m or shorter, or may be 50 m or shorter.

In the above embodiment, the temperature difference between the atmospheres is 1° C. or greater, more preferably 5° C. or greater, still more preferably 10° C. or greater. The temperature difference is preferably 50° C. or smaller.

The shift of the optical coherence tomographic image is preferably 100 μm or shorter, more preferably 50 μm or shorter, particularly preferably 30 μm or shorter.

The shift ($\Delta Z$) is defined by the following equation (A):

$$\Delta Z(\mu m) = dn/dT(1/°C.) \times L(m) \times 10^6 \times 2 \times \Delta t(°C.) \quad (A)$$

wherein dn/dT represents the temperature coefficient (1/° C.) of the refractive index of the optical fiber material; L represents the length (m) of the optical fiber; and $\Delta t$ represents the temperature difference (° C.) between the sample light path and the reference light path.

$\Delta Z$ refers to the shift in the optical distance.

In the case where the optical fiber material is quartz glass, the optical wavelength is 1.3 μm, and the temperature is around room temperature, dn/dT is about $1.9 \times 10^{-5}$ (1/° C.).

In the case of an OCT device including the sample light path on the probe end and the reference light path on the body end, the temperature difference between the atmosphere around the portion including the objective lens to be carried and the atmosphere around the portion not to be carried is almost directly reflected in the temperature difference $\Delta t$ between the optical paths. This causes a great shift $\Delta Z$ in a tomographic image obtained. In contrast, in the case of the OCT device of the disclosure, the temperature difference $\Delta t$ between the optical paths is significantly small even when the temperature difference is large between the atmosphere around the portion including the objective lens to be carried and the atmosphere around the portion not to be carried. This results in a significantly small shift $\Delta Z$.

Figure 3:
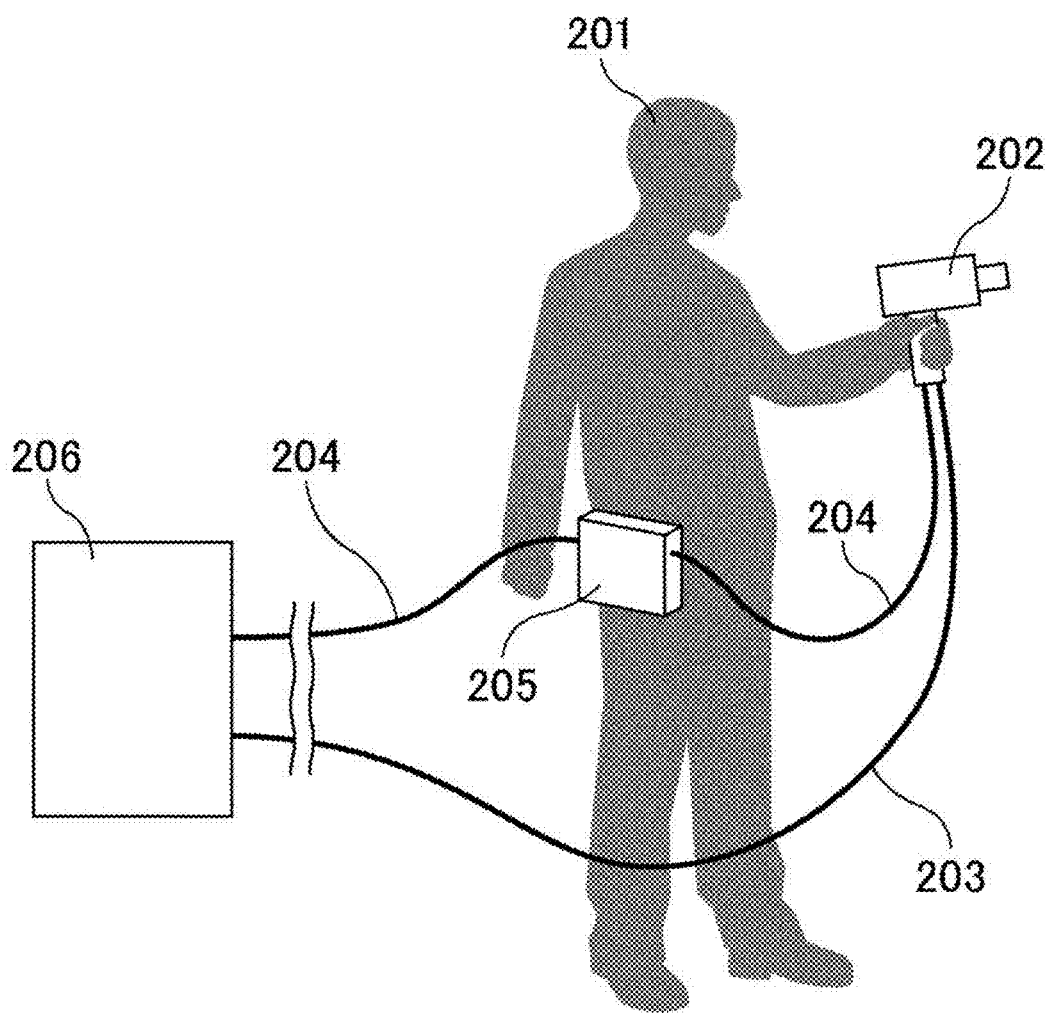
FIG. 3 is a schematic diagram of another example of the OCT device of the disclosure.

Another example (an example in which the portion including the objective lens is in a portable form) of the OCT device of the disclosure is shown in FIG. 3. The OCT device of the disclosure is not limited thereto.

In FIG. 3, a user 201 carries a probe 202 of the OCT device in one hand and carries a galvanometer mirror driver 205 for driving the galvanometer mirror in the probe 202 at the waist. The probe 202 is connected to a housing 206 of the OCT device via an optical fiber 203. The galvanometer mirror driver 205 is connected to the probe 202 and the housing 206 via respective electric wires 204.

The housing 206 contains a light source, a detector, a DAQ system, an arithmetic logic unit, and the like.

The OCT device of the disclosure is preferably configured such that the area in the plane direction to be imaged at an optical resolution of 10 μm or longer per tomographic imaging session using the following light source is 0.1 to 14 mm in length and 0.1 to 14 mm in width. This enables high-precision tomographic imaging over a wide area at one time (even with a different light source).

(Light Source)

High speed swept source available from Axsun Technologies (central wavelength: 1310 nm, sweep width: 100 nm, A-scan rate: 50 kHz, output: 25 mW, coherence length: 12 mm)

The OCT device of the disclosure may be used to perform optical coherence tomographic imaging of a sample. The disclosure also relates to an optical coherence tomography method using the aforementioned OCT device of the disclosure.

The optical coherence tomography method of the disclosure causes no difference in environmental conditions between the sample light path and the reference light path even in the case where a user carries the portion including the objective lens (e.g., the probe) to perform tomographic imaging. This results in a small shift in a tomographic image obtained. This method also enables tomographic imaging over a wide area at one time.

The OCT device and the optical coherence tomography method of the disclosure can be suitably applied to the whole range of optical coherence tomography regardless of the fields. As described above, they are less likely to cause a shift in a tomographic image even in the case where a portion of the OCT device is in a portable form and they enable tomographic imaging over a wide area at one time. Accordingly, the device and the method can be suitably used especially in the industrial field.

The disclosure relates to an optical coherence tomography device including an objective lens configured to focus light from a light source onto a sample, the optical coherence tomography device being configured to perform tomographic imaging of the sample based on interference between sample light, which is reflected light from the sample, and reference light, which is reflected light from a reference surface provided between the objective lens and the sample, the sample light and the reference light each being to pass through the objective lens, the objective lens being an Fθ lens.

The optical coherence tomography device is preferably configured to perform the tomographic imaging with a distance between the reference surface and the sample being 0 to 3 cm.

The reference surface is preferably a flat surface of a reference item containing at least one selected from the group consisting of $MgF_2$, $CaF_2$, quartz, and sapphire.

The sample light and the reference light are each preferably generated from the light emitted from the light source and passed through the objective lens.

The interference is preferably Fizeau interference.

The optical coherence tomography device preferably further includes a circulator configured to: output the light from the light source toward the objective lens; and output the sample light and the reference light passed through the objective lens toward a detector configured to detect the sample light and the reference light.

Preferably, the optical coherence tomography device further includes a coupler configured to split the light emitted from the light source into split light 1 to be used for generating the sample light and the reference light and split light 2 to be used for removing a DC component of an interference signal, wherein the split light 1 and the split light 2 have an intensity ratio of 90:10 to 99:1.

Preferably, the optical coherence tomography device is configured to perform the tomographic imaging while a user carries a portion comprising the objective lens.

Preferably, the portion including the objective lens to be carried and a portion not to be carried are connected via an optical fiber, and the light emitted from the light source as well as the sample light and the reference light are transmitted through the optical fiber.

Preferably, an optical coherence tomographic image obtained has a shift of 100 μm or smaller when the optical fiber has a length of 3 m or longer and an atmosphere around the portion including the objective lens to be carried and an atmosphere around the portion not to be carried have a temperature difference of 1° C. or greater.

The disclosure also relates to an optical coherence tomography method including using any of the aforementioned optical coherence tomography devices.

EXAMPLES

The disclosure is more specifically described below with reference to, but not limited to, examples.

Example 1

Figure 4:
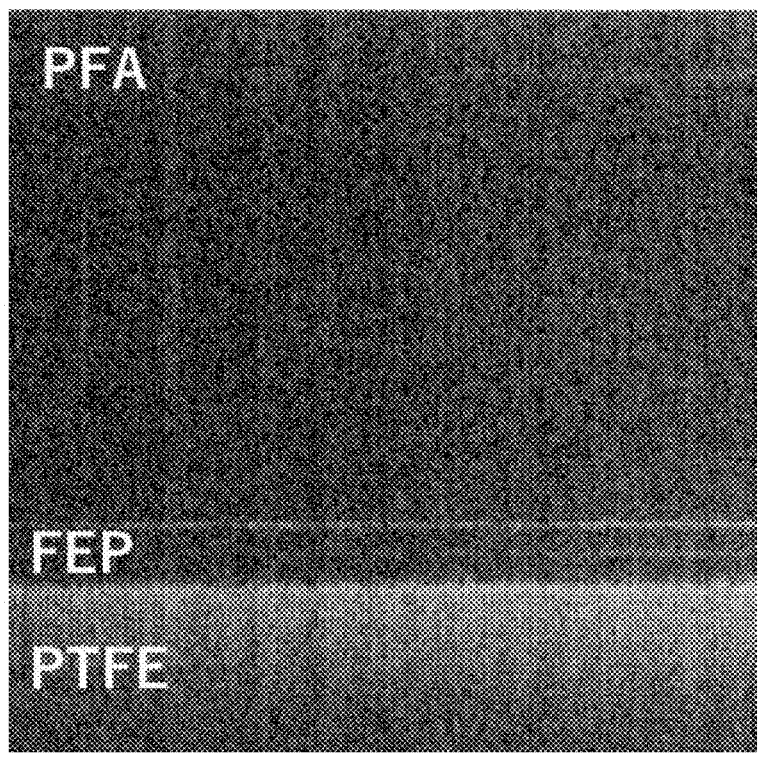
FIG. 4 is an OCT image obtained in Example 1.

A fluororesin sheet having a thickness of 7.8 mm, a length of 25 mm, and a width of 25 mm was prepared, which was a stack of a 3.1-mm-thick polytetrafluoroethylene (PTFE) layer, a 0.4-mm-thick tetrafluoroethylene-hexafluoropropylene copolymer (FEP) layer, and a 4.3-mm-thick tetrafluoroethylene-perfluoro (alkyl vinyl ether) copolymer (PFA) layer in the stated order. Using an OCT device having the structure shown in FIG. 2, OCT imaging of the fluororesin sheet was performed from the PFA layer end. The resulting tomographic image (length 8 mm× width 8 mm) is shown in FIG. 4.

The details of the OCT device and imaging conditions used are as follows.

OCT swept laser light source: central wavelength 1310 nm, sweep width 100 nm, A-scan rate 50 kHz, output 25 mW, coherence length 12 mm Objective lens: Fθ lens (trade name: LSM04, available from Thorlabs, Inc.), effective wavelength range (1250 to 1380 nm), effective focal length (54 mm)

Reference item: made of quartz glass, cylindrical shape, diameter 20 mmφ, length 20 mm Optical fiber: made of quartz glass, length 10 m Imaging temperature: 26° C.

Distance between reference surface and sample: 0 cm

Other imaging conditions: brightness 100, contrast ratio 30

Comparative Example 1

Figure 5:
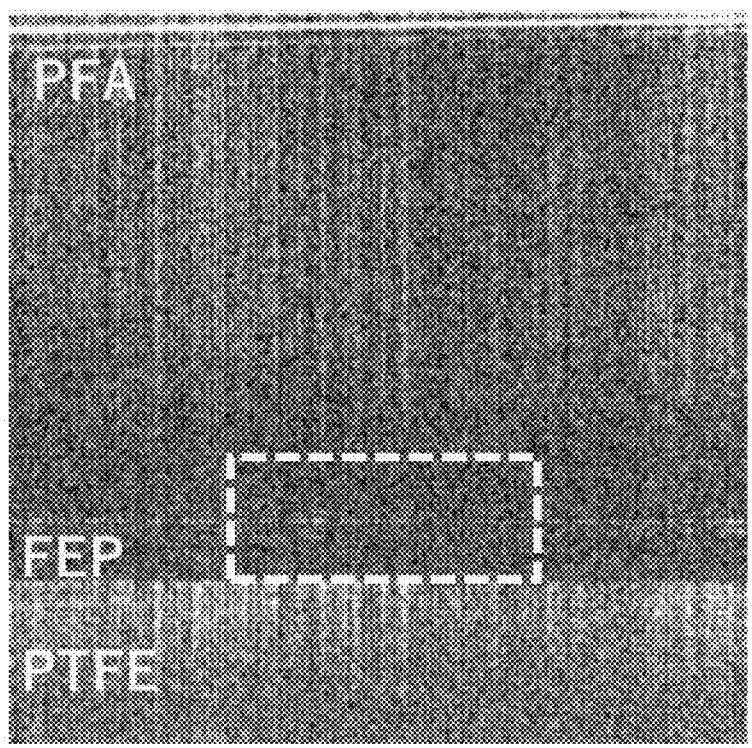
FIG. 5 is an OCT image obtained in Comparative Example 1.

OCT imaging was performed as in Example 1 except that the objective lens was changed to an achromatic lens (trade name: AC254-050-C, available from Thorlabs, Inc., effective wavelength range: 1050 to 1700 nm, effective focal length: 50 mm), which is not an Fθ lens. The resulting tomographic image (length 8 mm×width 8 mm) is shown in FIG. 5.

In FIG. 4, the whole tomographic image is clear and uniform. In FIG. 5, the image excluding the portion enclosed by dotted lines includes significant noise and has a narrow effective visual field (shows a failure in tomographic imaging over a wide area).

Comparative Example 2

Figure 6:
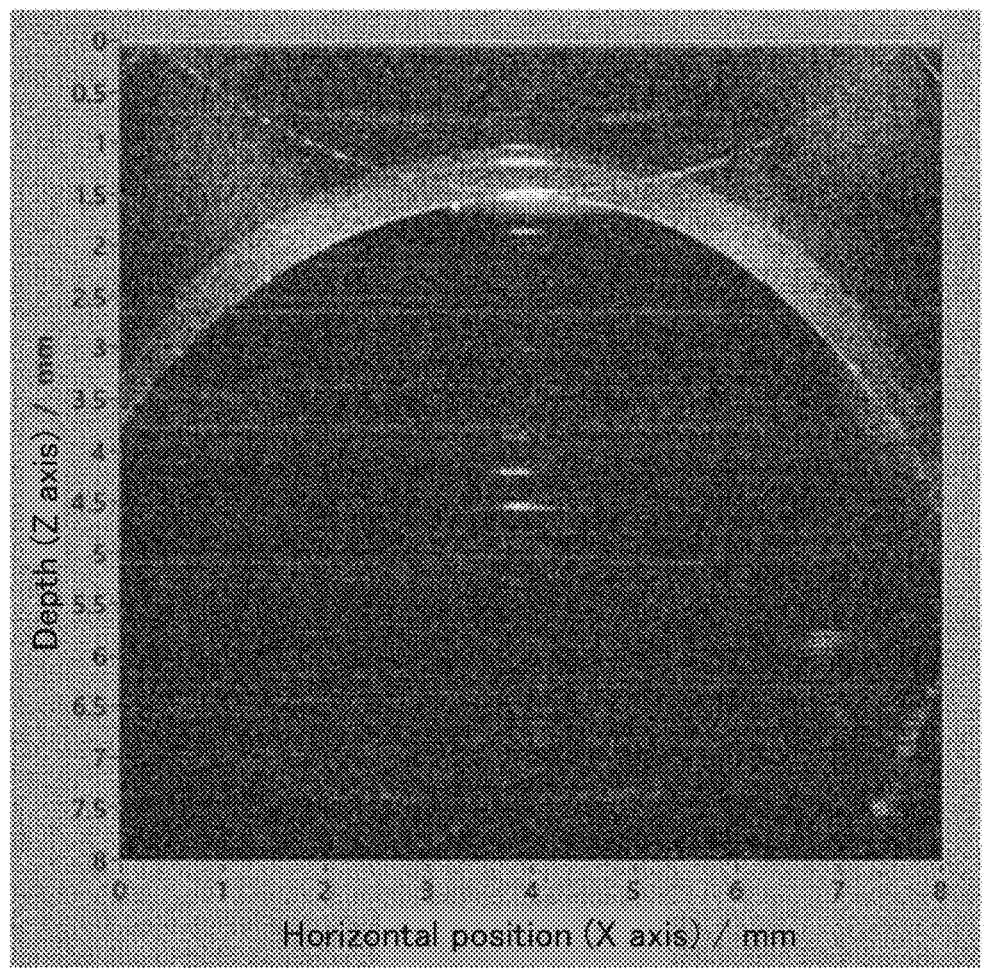
FIG. 6 is an OCT image obtained in Comparative Example 2.

An OCT device having the structure shown in FIG. 1 was used and the optical fiber of the sample arm alone was heated to 40° C. using a dryer. Then, OCT imaging was performed in the cross-sectional direction of a fluororesin tube having an outer diameter of 12 mm and an inner diameter of 8 mm. The resulting tomographic image is shown in FIG. 6.

The details of the OCT device and imaging conditions used are as follows.

OCT swept laser light source: central wavelength 1310 nm, sweep width 100 nm, A-scan rate 50 kHz, output 25 mW, coherence length 12 mm Objective lens: Fθ lens (trade name: LSM03, available from Thorlabs, Inc.), effective wavelength range (1250 to 1380 nm), effective focal length (36 mm)

Optical fibers (sample arm, reference arm): made of quartz glass, length 4 m

Imaging temperature: 26° C.

Other imaging conditions: brightness 100, contrast ratio 30

Reference Example 1

OCT imaging was performed as in Comparative Example 2 except that the optical fiber of the sample arm was not heated. The resulting tomographic image is shown in FIG. 7.

Figure 7:
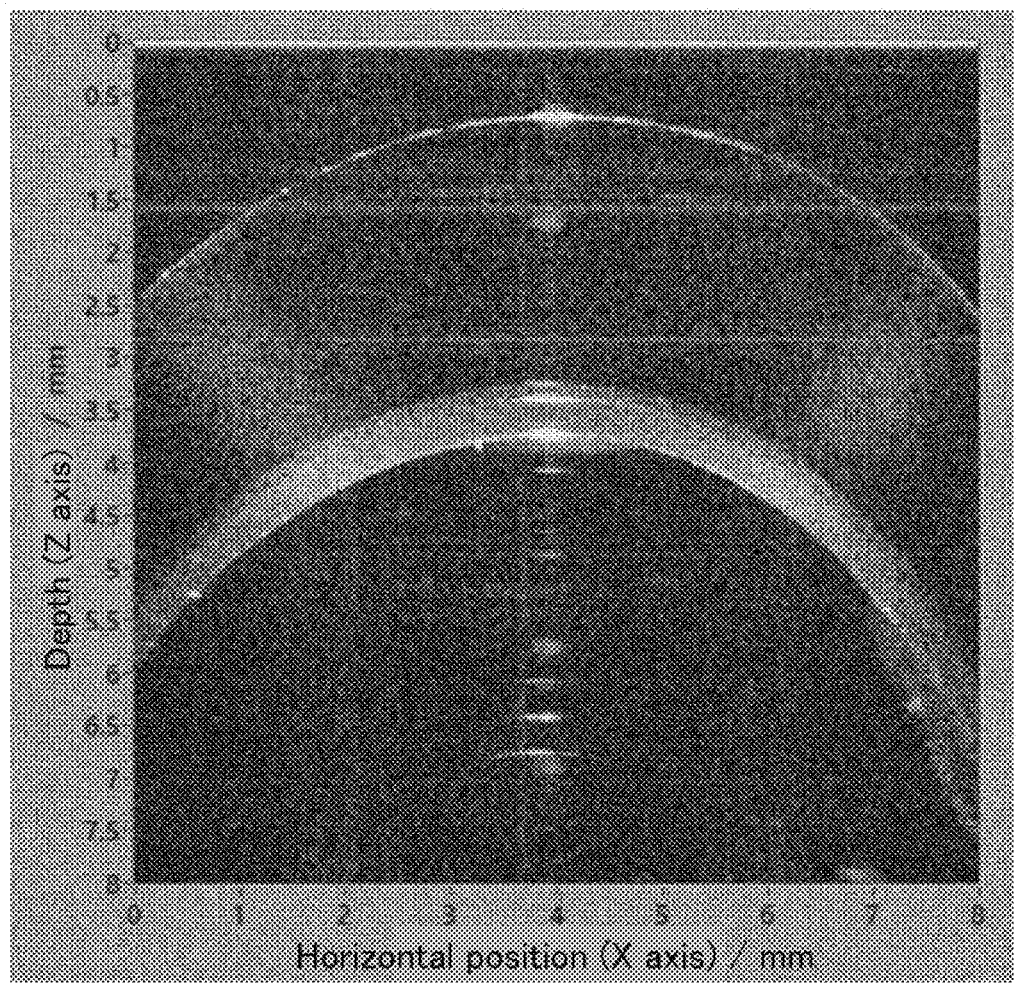
FIG. 7 is an OCT image obtained in Reference Example 1.

In FIG. 6 obtained under a temperature difference between the arms, the tomographic image of the tube is drifted upwards in the depth direction by 2 mm or greater compared to FIG. 7 and the portion corresponding to the tube surface layer protrudes from the image. Further, FIG. 6 includes an artifact (an inverted arch at the upper portion of the image), which is reflection noise.

REFERENCE SIGNS LIST

10: OCT device
11: light source 12, 17: coupler
13, 15: circulator
14: reference mirror
16: sample
18: photodetector
100: OCT device
101: frequency-scanning light source
102: coupler
103: circulator
104: probe
105: collimator
106: galvanometer mirror
107: objective lens
108: reference item
109: reference surface
110: sample
111: galvanometer mirror driver
112: variable optical attenuator
113: differential photodetector amplifier
114: PC
115: mobile display
201: user
202: probe
203: optical fiber
204: electric wire
205: galvanometer mirror driver
206: housing

What is claimed is:

1. An optical coherence tomography device comprising:
an objective lens configured to focus light from a light source onto a sample,
wherein the optical coherence tomography device is configured to perform tomographic imaging of the sample based on interference between sample light, which is reflected light from the sample, and reference light, which is reflected light from a reference surface provided between the objective lens and the sample,
the sample light and the reference light each pass through the objective lens,
the objective lens is an Fθ lens, and
the reference surface is a flat surface of a reference item satisfying the following relation (3):

$$n \times WD > nd > n \times Z_{max} \quad (3)$$

wherein n represents a refractive index of the reference item; WD represents a working distance of the OCT device; and nd represents an optical thickness of the reference item; and $Z_{max}$ represents a measurable distance expressed by the following relation (2):

$$Z_{max} = c/(4\delta f) \quad (2)$$

wherein c represents the speed of light; and $\delta f$ represents a frequency interval of OCT interference signal sampling.

2. The optical coherence tomography device according to claim 1,
wherein the optical coherence tomography device is configured to perform the tomographic imaging with a distance between the reference surface and the sample being 0 to 3 cm.

3. The optical coherence tomography device according to claim 1,
wherein the reference item contains at least one selected from the group consisting of $MgF_2$, $CaF_2$, quartz, and sapphire.

4. The optical coherence tomography device according to claim 1,
wherein the sample light and the reference light are each generated from the light emitted from the light source and passed through the objective lens.

5. The optical coherence tomography device according to claim 1,
wherein the interference is Fizeau interference.

6. The optical coherence tomography device according to claim 1, further comprising a circulator configured to:
output the light from the light source toward the objective lens; and
output the sample light and the reference light passed through the objective lens toward a detector configured to detect the sample light and the reference light.

7. The optical coherence tomography device according to claim 1, further comprising a coupler configured to split the light emitted from the light source into a first split light to be used for generating the sample light and the reference light and a second split light to be used for removing a DC component of an interference signal,
wherein the first split light and the second split light have an intensity ratio of 90:10 to 99:1.

8. The optical coherence tomography device according to claim 1,
wherein the optical coherence tomography device is configured to perform the tomographic imaging while a user carries a portion comprising the objective lens.

9. The optical coherence tomography device according to claim 8,
wherein the portion comprising the objective lens to be carried and a portion not to be carried are connected via an optical fiber, and
the light emitted from the light source as well as the sample light and the reference light are transmitted through the optical fiber.

10. The optical coherence tomography device according to claim 9,
wherein the optical fiber has a length of 3 m or longer and an atmosphere around the portion comprising the objective lens to be carried and an atmosphere around the portion not to be carried have a temperature difference of 1° C. or greater, and
an optical coherence tomographic image obtained has a drift size of 100 μm or smaller.

11. An optical coherence tomography method, comprising: acquiring a tomographic image of an object using the optical coherence tomography device according to claim 1.

* * * * *